(12) United States Patent
Britton et al.

(10) Patent No.: US 8,154,273 B2
(45) Date of Patent: Apr. 10, 2012

(54) DETECTING AND HANDLING COINCIDENCE IN PARTICLE ANALYSIS

(75) Inventors: Ted W. Britton, Sunrise, FL (US); Jiuliu Lu, Homestead, FL (US); Jeffrey L. Rose, Pembroke Pines, FL (US)

(73) Assignee: Beckman Coulter, Inc., Brea, CA (US)

( * ) Notice: Subject to any disclaimer, the term of this patent is extended or adjusted under 35 U.S.C. 154(b) by 664 days.

(21) Appl. No.: 12/249,473

(22) Filed: Oct. 10, 2008

(65) Prior Publication Data

US 2010/0090677 A1    Apr. 15, 2010

(51) Int. Cl.
*G01N 27/00* (2006.01)
(52) U.S. Cl. ..................... 324/71.4; 324/71.1
(58) Field of Classification Search .................. 324/71.1, 324/71.4
See application file for complete search history.

(56) References Cited

U.S. PATENT DOCUMENTS

| | | | |
|---|---|---|---|
| 4,263,508 A | | 4/1981 | Leary et al. |
| 4,981,580 A | | 1/1991 | Auer |
| 5,286,452 A | * | 2/1994 | Hansen ........................... 422/73 |
| 5,616,501 A | | 4/1997 | Rodriguez et al. |
| 5,998,212 A | | 12/1999 | Corio et al. |
| 6,463,785 B1 | * | 10/2002 | Kline-Schoder et al. ..... 73/19.03 |
| 6,518,747 B2 | * | 2/2003 | Sager et al. .................... 324/204 |
| 7,417,418 B1 | * | 8/2008 | Ayliffe ........................... 324/71.1 |
| 2003/0235919 A1 | | 12/2003 | Chandler |
| 2006/0015291 A1 | | 1/2006 | Parks et al. |
| 2006/0203226 A1 | | 9/2006 | Roche et al. |
| 2007/0020721 A1 | * | 1/2007 | Yoshida et al. ................. 435/34 |
| 2007/0047674 A1 | | 3/2007 | Rose |
| 2008/0158561 A1 | | 7/2008 | Vacca et al. |
| 2008/0204719 A1 | * | 8/2008 | Trainer ........................... 356/73 |
| 2008/0215297 A1 | | 9/2008 | Goebel et al. |
| 2008/0221812 A1 | | 9/2008 | Pittaro et al. |
| 2008/0248966 A1 | | 10/2008 | Hansen et al. |

OTHER PUBLICATIONS

International Search Report and Written Opinion issued in International Appl. No. PCT/US2009/059363 mailed on Feb. 1, 2010, 13 pgs.

* cited by examiner

*Primary Examiner* — Jeff Natalini
(74) *Attorney, Agent, or Firm* — K&L Gates LLP; Louis C. Cullman; Andrew L. Reibman

(57) ABSTRACT

Methods and systems substantially eliminate data representative of coincident events from particle analyzer data. A fluid sample containing particles for analysis is prepared. Using an electrical or optical measurement device, signals are sensed. Each signal corresponds to events detected in a sub-sample of the fluid sample flowing through a measurement region in the particle analyzer. The existence of coincidence in the events is determined based on measuring a peak and first and second points of each of the signals. The first and second points have a signal value corresponding to a predetermined portion of the peak. Results data based upon the coincident events and non-coincident events is generated. The results data is then analyzed. In various examples, the method is applicable to a variety of particle types, and may be implemented on different types of particle analyzers including hematology analyzer and flow cytometers.

37 Claims, 20 Drawing Sheets

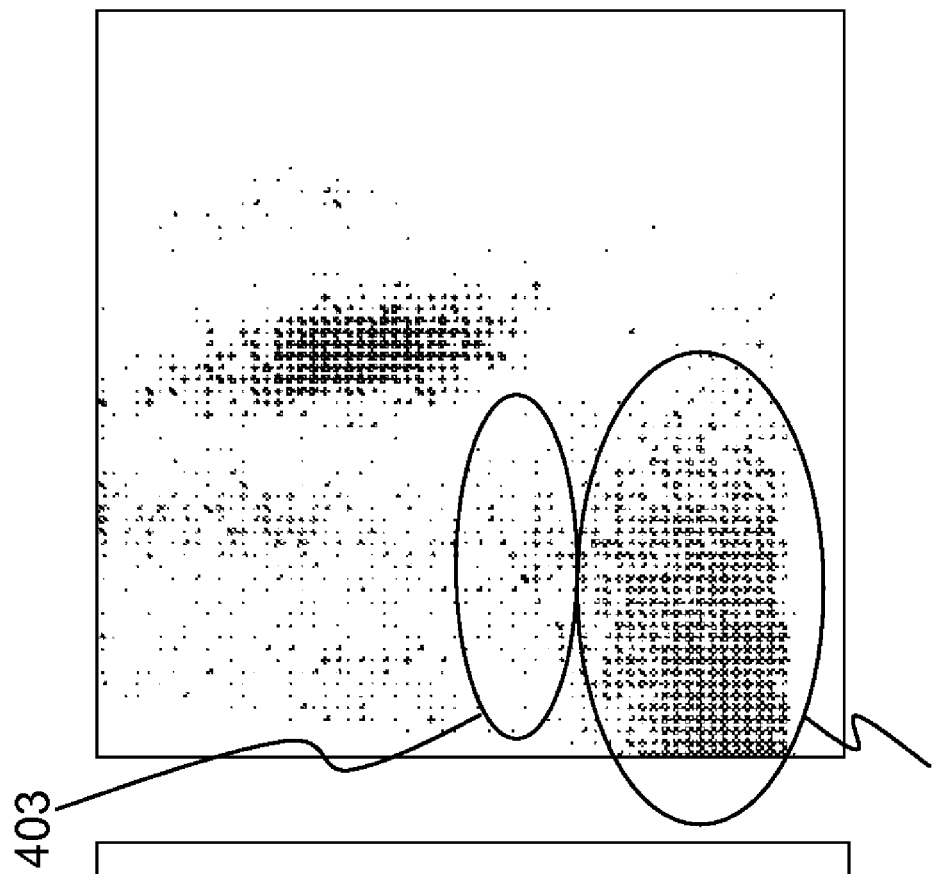
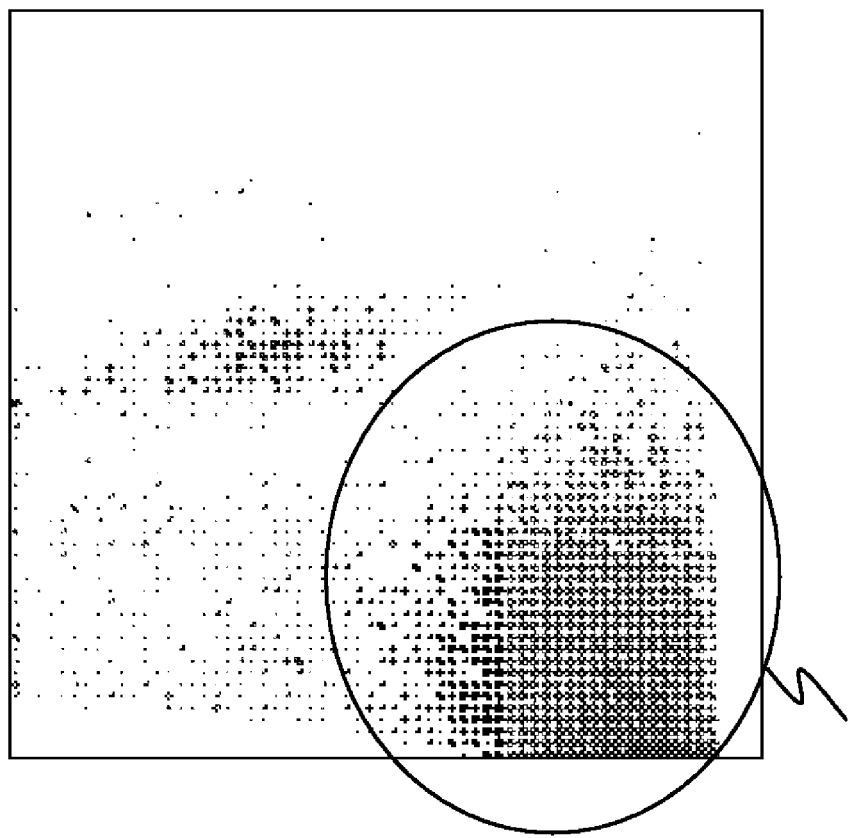

DETECTING AND HANDLING COINCIDENCE IN PARTICLE ANALYSIS

FIELD

This invention relates in general to the analysis of particles using a particle analyzer, and more particularly to detecting and handling, when overlapping particles are measured at substantially the same time, e.g., coincidence, in data generated by a particle analyzer.

BACKGROUND

Particle analyzers are used to analyze biological and industrial samples to determine the count and/or distribution of one or more types of particles contained in the samples. In the medical industry, in order to analyze or research bodily fluids, particle analyzers including hematology analyzers and flow cytometers can be used. For example, hematology analyzers and flow cytometers are used to measure and differentiate between different types of blood cells by capturing and analyzing signals. The signals are produced by using probes interacting with the sample as blood cells pass through a small aperture or measurement region. In general, a sample of blood is diluted in a liquid before being directed to flow through a flow cell that contains the measurement region. One or more sensors or detectors are arranged to detect various characteristics of the blood cells that pass through the measurement region as the blood cells interact with the probe.

During the measurement, the diluted blood sample is injected into the flow cell at a substantially constant rate. A reference reading is obtained when no blood cell is in the measurement region of the flow cell. When a blood cell is present, the physical properties of the measurement region are altered. Therefore, the signal differs from the respective reference signal when a cell is in the measurement region. The deviation of sensor readings gradually increases as the blood cell flows towards the midpoint of the measurement region and then gradually decreases as the blood cell flows away from the midpoint.

It is common practice to collect and analyze a maximum signal (i.e., peak) caused by the interaction of the blood cell and one or more measurement parameters, for example, direct current (DC) which obeys the Coulter Principle, Radio Frequency (RF), Light Scatter (LS), Axial Light Loss (ALL), ultrasound, etc. In general, the peak of the signal is a well-defined function of the interaction between a type of blood cell and measurement parameter, i.e., type of stimulus and sensor. For example, the peak of a signal generated by a DC measurement indicates the volume of the cell, and the cell may be categorized based on the volume. Cells are counted and cell types are identified based on one or more measurement parameters.

Applications based on the above relationship rely on blood cells passing through the measurement region one at a time. If multiple blood cells pass through the measurement region simultaneously (i.e., coincidence) the maximum deviation between the captured signal and the reference signal is no longer a well-defined function of the interaction between a type of blood cell and measurement parameters. Moreover, in the presence of severe coincidence, histograms accumulated from received signals can be distorted and analytic results may be compromised.

Conventional approaches to address coincidence include the application of statistical methods to particle data counts and histograms to compensate for the expected coincidence errors. Another method to detect coincidence is based on the area and the peak of a signal generated when a particle passes through a measurement region. However, statistical methods may not yield accurate coincidence elimination due to inherent estimation errors. Also, methods relying on a ratio of area to peak of a signal generated by a particle may not be sufficiently accurate for particles of varied sizes and shapes. Area-to-peak-based measures may also yield inconsistent results when particles pass through the measurement region at various orientations.

Therefore, what are needed are improved methods and systems to identify and compensate for data representative of coincidence in particle analyzer data.

SUMMARY

Methods and systems for substantially eliminating data representative of coincident events from particle analyzer data are presented. In one embodiment, there is provided a method of analyzing particles in a particle analyzer including at least the following steps. A fluid sample containing particles for analysis is prepared. Using an electrical or optical measurement device, signals are sensed where each signal corresponds to one or more events detected in a sub-sample of the fluid sample flowing through a measurement region in the particle analyzer. The existence of coincident events is determined based on measuring a peak and first and second points of each of the signals where the first and second points have a signal value corresponding to a predetermined portion of the peak. Results data based upon identified coincident events and non-coincident events are generated. The results data is then analyzed.

In various examples, the method is applicable to the analysis of a wide variety of particles. Also, in various examples, the method can be implemented in particle analyzers including hematology analyzers and flow cytometers.

Another embodiment is a system having at least a particle detector and an analyzer. The particle detector is configured to sense signals using an electrical or optical device where each signal corresponds to events detected in a sub-sample of the fluid sample flowing through a measurement region in the particle detector. The analyzer is configured to determine the existence of coincident events based on measuring a peak, and first and second points of each of the signals, where the first and second points have a signal value corresponding to a predetermined portion of the peak, to generate results data based upon the coincident events and non-coincident events.

Further features and advantages of the present invention, as well as the structure and operation of various embodiments thereof, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

Further features and advantages of the present invention, as well as the structure and operation of various embodiments thereof, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

FIGS. 4A and 4B illustrate scatter plots, respectively, without and with coincidence identification and handling applied, according to an embodiment of the present invention.

Figure 1A:
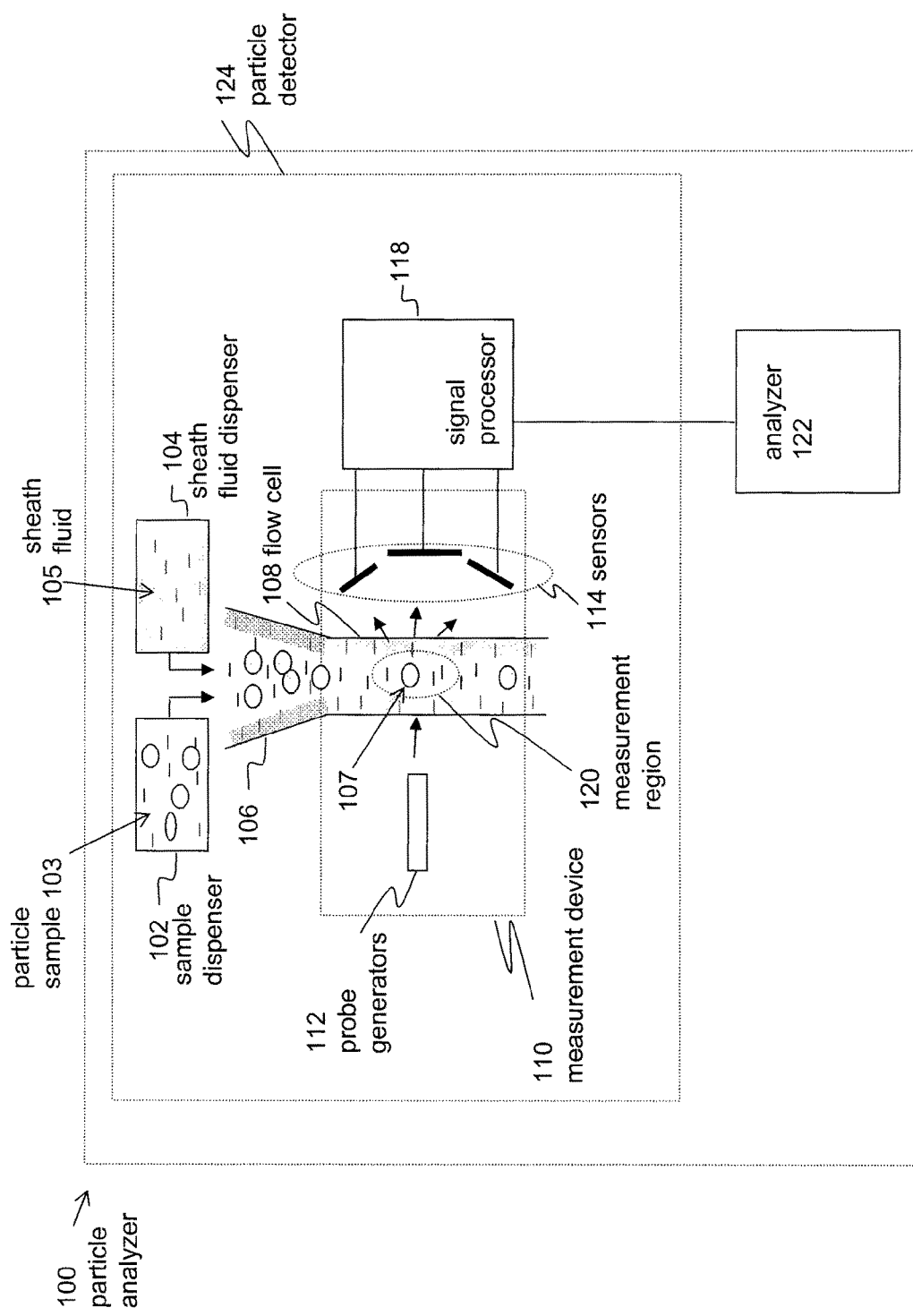
FIG. 1A is a system according to an embodiment of the present invention.

The features and advantages of the present invention will become more apparent from the detailed description set forth below when taken in conjunction with the drawings. In the drawings, like reference numbers generally indicate identical, functionally similar, and/or structurally similar elements. Generally, the drawing in which an element first appears is indicated by the leftmost digit(s) in the corresponding reference number.

DETAILED DESCRIPTION

The present invention is directed to detection and handling of coincident events. This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Overview

As discussed above, when coincidence, e.g., when multiple particles are in a measuring area at a same time, occurs during particle analysis, data representing particle counts and particle distributions may be distorted. The methods and systems according to embodiments disclosed below yield more accurate particle analyzer data by eliminating or otherwise accounting for coincidence events.

Exemplary environments in which embodiments of this invention may be practiced include flow cytometers and hematology analyzers, such as Beckman Coulter's FC 500™ and Gen·S™ System respectively. The Gen·S™ System, for example, uses the Coulter proprietary Volume, Conductivity, and Scatter (VCS) and Axial Light Loss (ALL) technology to probe hydrodynamically focused cells within a flow cell. VCS uses multiple independent energy sources that work in concert with each other to probe cells: a low frequency direct current power source to measure volume, a high frequency power source to measure conductivity, and laser light sources to measure scatter and axial light loss.

The volume measurement is performed using the Coulter Principle of electrical impedance to physically measure the volume that the entire cell displaces in an isotonic diluent. This method accurately sizes all cell types regardless of their orientation in the light path. Alternating current in the radio frequency (RF) range is used to collect information about cell size and internal structure, including chemical composition and nuclear volume.

Laser and multiple-angle light scatter sensors or detectors provide information about a cell's internal structure, granularity, and surface morphology. In addition, VCS instruments use the highly accurate DC measurement of volume, to obtain other measurements that are adjusted for cell size from conductivity and scatter. For example, U.S. Pat. No. 5,616,501 (to Rodriguez et. al), which is hereby incorporated by reference in its entirety, contains an exemplary detailed description of a particle analyzer and the use of VCS technology. It should be noted, however, that the teachings discussed herein are not limited to devices using VCS technology. For example, the embodiments of the invention are also applicable to Multi-sizer™ 3 Coulter Counter®, a particle analyzer with numerous applications in addition to biological sample analysis.

FIG. 1A illustrates components of a particle analyzer 100, according to one embodiment of the present invention. FIG. 1A is for illustrative purposes only, and it should be understood that particle analyzers can include more or less modules, different modules, and different designs than shown in FIG. 1A. Particle analyzer 100 includes an analyzer 122 and a particle detector 124. Particle detector 124 includes sample dispenser 102, a sheath fluid dispenser 104, a chamber 106, a flow cell 108, a measurement device 110, probe generators 112, sensors 114, a signal processor 118, and a measurement region 120.

In the example shown, sample dispenser 102 includes a particle sample 103 prepared according to the requirements of a desired analysis or test. For example, a sample of blood may be diluted with a diluent to a predetermined degree of cell concentration. The type of diluent and the degree of dilution differ according to the test being run, e.g., white blood cell (WBC) analysis requires less dilution than red blood cells (RBC) because the number of WBC in a sample is low compared to RBC. Sheath fluid dispenser 104 holds a sheath fluid 105 such as, for example, saline. The sheath fluid 105 causes the diluted particle sample 103 to be constrained near the axis of flow within the sheath fluid in flow cell 108. The diluted particle sample 103 from particle sample dispenser 102 and the sheath fluid 105 from sheath fluid dispenser 104 join in chamber 106 to form a focused fluid sample stream for analysis. The combined flow rates of the sample and sheath fluids create a predetermined constant flow rate into flow cell 108. For example, flow cell 108 can be a tube of a small diameter designed for particles 107 constrained by the sheath fluid 105 to pass through. The arrival times of individual particles 107 in measurement region 120 are affected by a number of factors including sample particle diameters, sample flow rate, the combined flow rate of the sample and sheath fluid, and the concentration of particles in the sample.

In this example, measurement device 110 is positioned within particle analyzer 100, such that one or more sensors may be employed to sense particles 107 flowing through flow cell 108. For example, probes 112 and one or more sensors 114 can be positioned within measurement device 110 substantially transversely to flow cell 108. In various examples, probes 112 and sensors 114 employ one or more of electrical or optical measurement devices to detect particles 107 in flow cell 108, specifically particles flowing through a measurement region 120. For example, one set of paired probes 112 and sensors 114 can employ a DC measurement parameter to measure the volume of a particle 107 passing through measurement region 120. Another set of paired probes 112 and sensors 114 can employ an RF measurement parameter to measure the conductivity characteristics of a particle 107 passing through measurement region 120. Yet another set of probes 112 and sensors 114 can employ a light measurement parameter to measure the light scatter and light loss characteristics of a particle 107 passing through measurement region 120. Additionally, or alternatively, in other embodiments of the present invention, probes 112 and sensors 114 can include an acoustic measurement device where, for example, an ultrasound measurement parameter is used to detect various characteristics of a particle 107 as it passes through measurement region 120.

Further, in the example shown, sensors 114 are coupled to a processing device 118, such as a signal processor. Sensors 114 convert detected electrical or optical measurements to corresponding electrical signal pulses that can be processed in signal processor 118. For example, for each particle 107 passing through measurement region 120, electrical signal pulses corresponding to a sequence of measurements are collected, for example, in signal processor 118. From these electrical signal pulses, a complete signal is produced that is illustrative of the measurements captured for one measurement parameter while a particle is flows through the measurement region (see, e.g., FIGS. 1B and 1C). A time duration of the signal is based on when the particle enters the measurement region through when the particle exits from the measurement region. In embodiments of the present invention, signal processor 118 may perform additional processing of each signal to derive one or more parameters describing the particle that was detected.

In this example, the detection of a particle 107 within measurement region 120 is referred to as an event. Also, an event, specifically, a coincident event, is generated when more than one particle 107 is in the measurement region 120 substantially simultaneously, i.e., when a coincidence occurs. Thus, signal processor 118 analyzes the derived signal corresponding to each detected event. The analyzed signals for the detected events are then transmitted to analyzer 122. In one example, analyzer 122 may be located in a computer coupled to particle detector 124, such as an implementation shown in FIG. 18. It should be noted that analyzer 122 can either be part of the particle analyzer 100 comprising particle detector 124, or be positioned remotely from particle analyzer 100 and connected through a wired or wireless communication medium such as, but not limited to, Ethernet or WIFI.

In one example, signal generation and event detection is performed separately for each active electrical or optical measurement parameter. For example, analyzer 122 can receive event data corresponding to each measurement parameter that is active. Analyzer 122 can then analyze the received event data to determine one or more counts, particle subpopulations, or other characteristics corresponding to the particle. In one embodiment of the present invention, analyzer 122 can cause or control the display of a scatter plot of the received events.

Figure 1B:
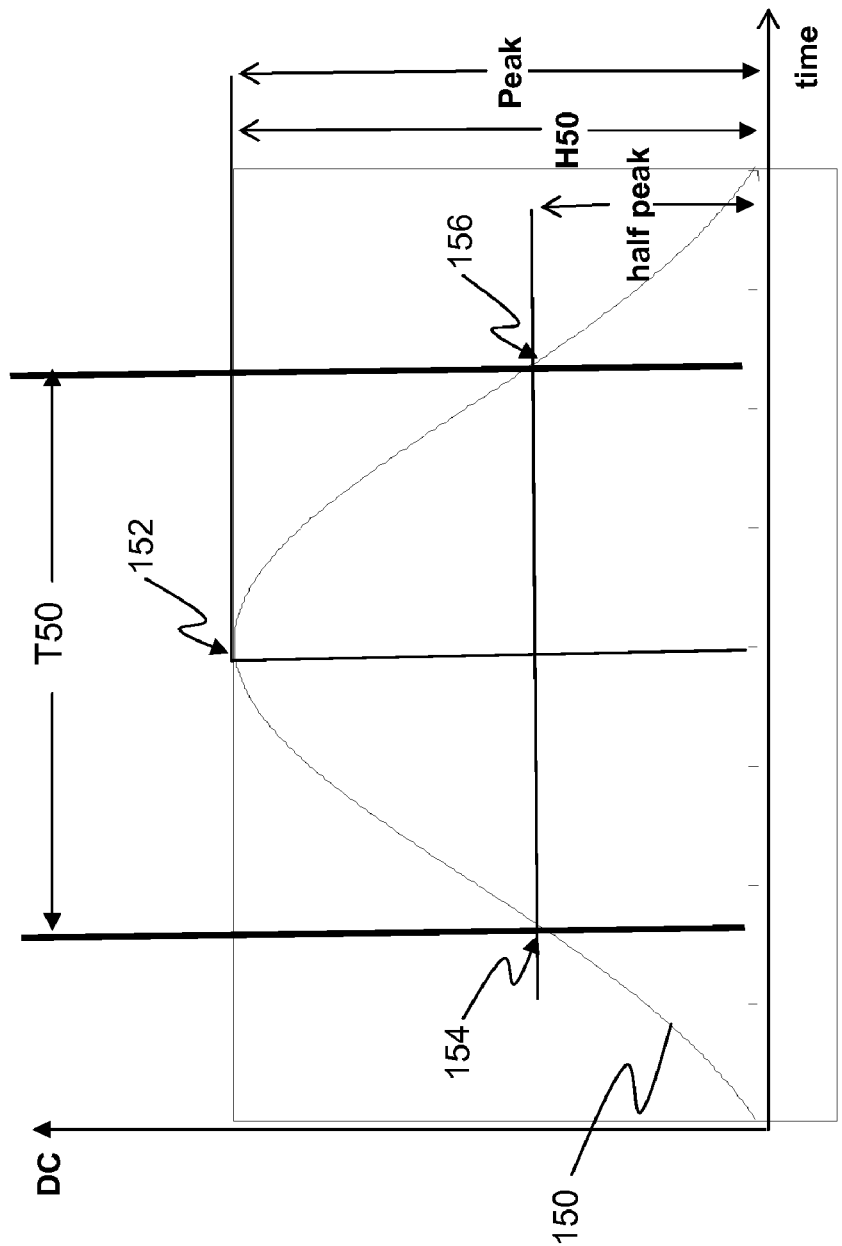
FIG. 1B illustrates a graphical representation of a signal captured during traversing of a measurement region by a particle, according to an embodiment of the present invention.

FIG. 1B illustrates a graphical representation of a signal 150 corresponding to captured signal measurements occurring during a time period that a particle travels from an entrance to an exit of a measurement region, according to one embodiment of the present invention. As the particle enters the measurement region, the particle only minimally interacts with a measuring device, producing a low intensity signal. The value of the signal gradually increases, reaching a peak 152 when the particle passes through the midpoint of the measurement region. After passing through the midpoint, the value of the signal gradually decreases as the particle exits the measurement region. Various parts of signal 150 can be used to determine characteristics of the particle, for example first and second half-peak points 154 and 156, midpoint of the half-peak lines H50, and other points. A time interval T50 between half-peak points 154 and 156 is also determinative of characteristics of the particle.

Coincident particles, i.e., when more than one particle is simultaneously present within measurement region 120, generally cause distortions in the corresponding signal. In some cases, the distortion of the signal can result in erroneous determinations regarding characteristics of the particles. The frequency of coincidence generally increases with the concentration of particles in the sample being analyzed.

Ideally, each individual particle 107 will independently pass through the midpoint of the physical measurement region 120 at a constant velocity, thereby creating a symmetrical unimodal signal. In this case, the peak measurement of the signal represents the maximum of the particle's interaction with the corresponding measurement parameter, and is related mathematically to some corresponding particle properties. A specific case is that the DC peak measurement is directly proportional to particle volume according to the Coulter Principle. However, when more than one particle 107 substantially simultaneously exists within the measurement region 120, i.e., there is, coincidence, the expected relation of the signal peak measurement to particle characteristics is confounded. The reason is that the observed signal of coincident particles is, in general, the superposition of the signals corresponding to the individual particles.

In one example, if the coincident particles traverse the measurement region substantially simultaneously, individual signals can overlap such that the resulting signal may be a symmetrical unimodal signal whose peak is equal to the sum of the individual peaks.

In another example, if two coincident particles pass through the measurement region separately, one passing before the other, but both being within the measurement region simultaneously, the resulting signals can range from being unimodal (before-bifurcation coincidence) to bimodal (after-bifurcation coincidence), which produces a signal having an M-shape.

Figure 1C:
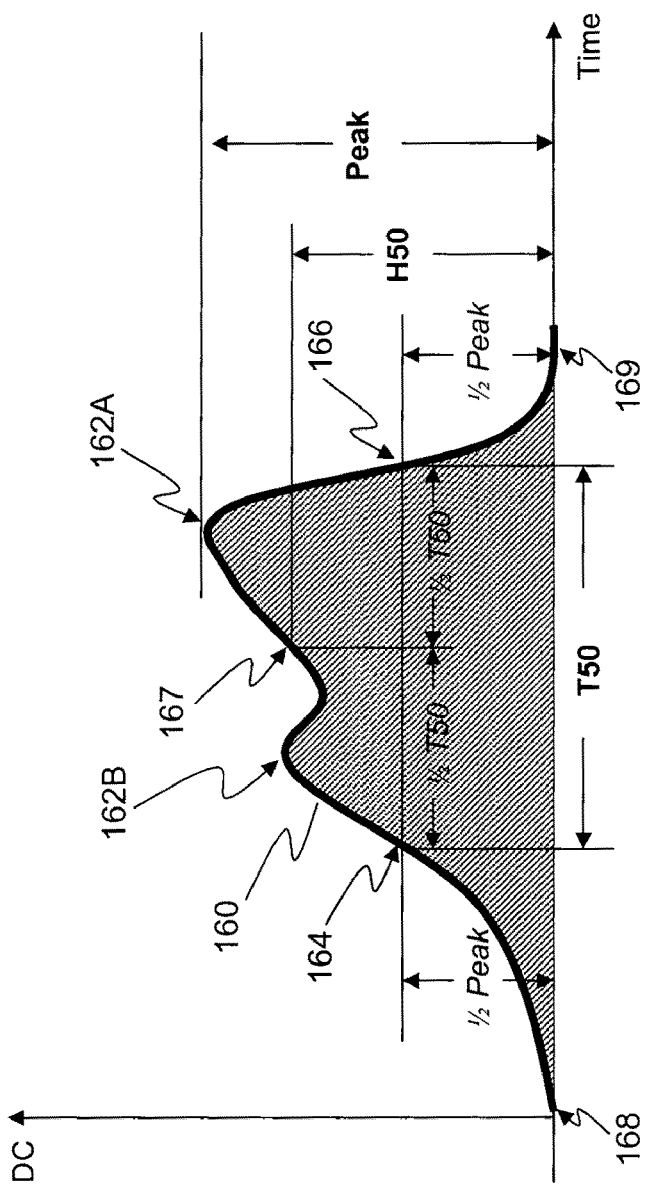
FIG. 1C illustrates a graphical representation of a signal captured during traversing of a measurement region substantially simultaneously by more than one particle, according to an embodiment of the present invention.

FIG. 1C illustrates a graphical representation of a signal 160 captured during traversing of a measurement region substantially simultaneously by more than one particle, according to an embodiment of the present invention. Starting at a time 168 when the first of the coincident particles enters measurement region 120, signal 160 gradually increases in value as the coincident particles approach the midpoint of measurement region 120 and gradually decreases in value when the particles have passed the midpoint until a time 169 when they exit measurement region 120. As each coincident particle approaches the midpoint of measurement region 120, a respective peak (e.g., 162A and 162B) can be observed, yielding an M-shape to signal 160. If the particles were perfectly coincidental (i.e., completely overlapping each other) then the resulting signal would have only one peak with a higher value than a peak associated with either particle alone.

As seen in FIG. 1C, distortions of the signal shape may vary depending on the temporal interval between the coincident particles, which may prevent accurate measurements of the individual signal characteristics. In general, when coincidence occurs, the instrument registers a smaller number of particles and more importantly the peak measurement may no longer be accurate. Consequently, the coincident particles appear as noise in scatter plots and histograms, for example, in scatter plots of a 5-part Differential. Thus in cases when the particle concentration is high and coincidence is prevalent, scatter plots and histograms based on the detected, processed, and analyzed data can be substantially distorted. The distortion may cause erroneous gating, accuracy, and flagging results.

Figure 2B:
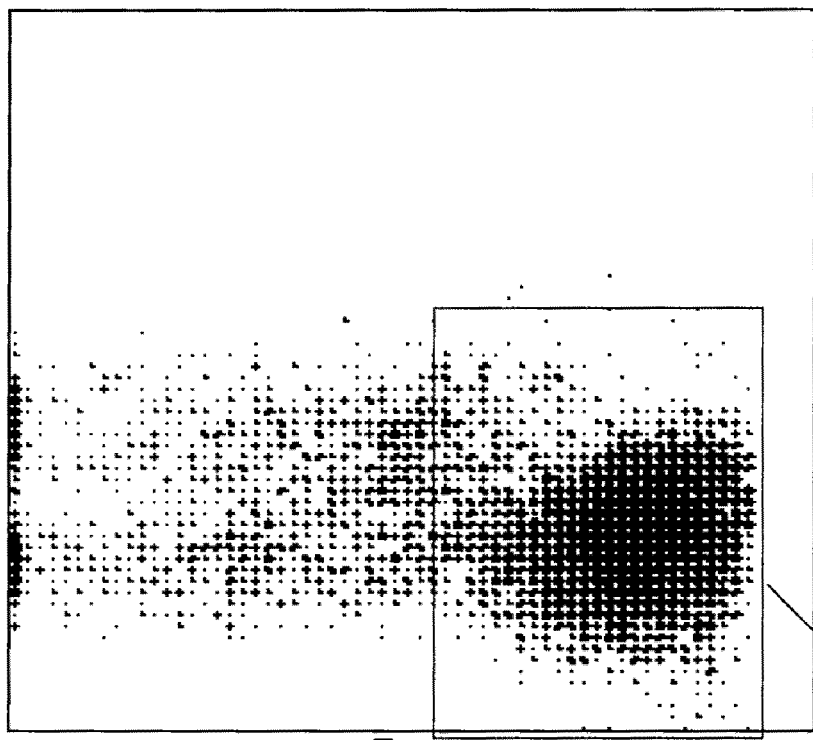
FIGS. 2A and 2B show the scatter pattern, respectively, without and with coincidence identification and handling, according to an embodiment of the present invention.
Figure 2A:
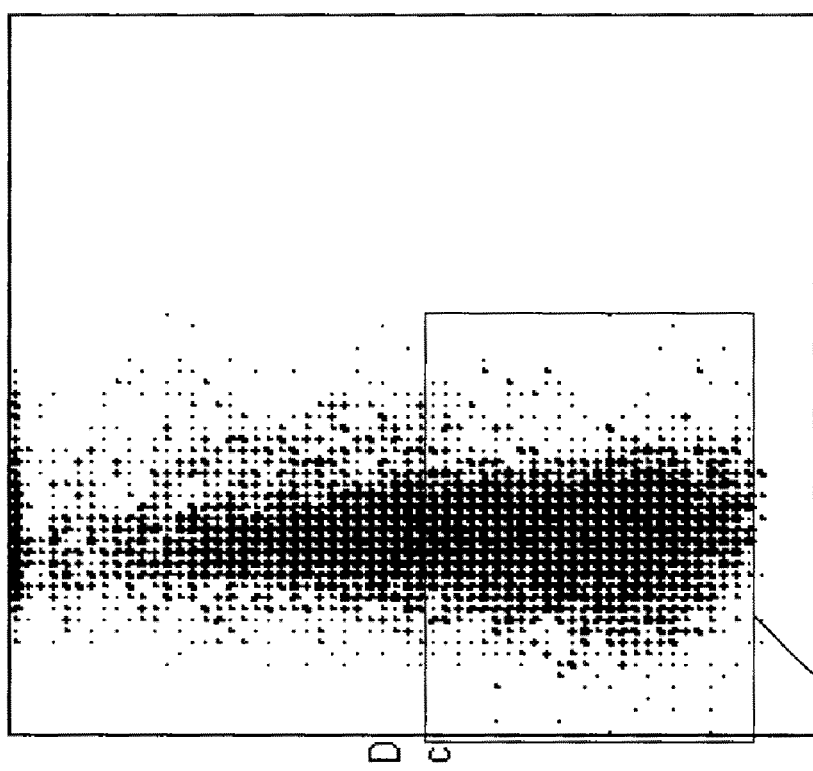

FIGS. 2A and 2B illustrate an improvement that can occur in displaying of data in a scatter plot with coincidence detection and handling using an embodiment of the present invention. FIG. 2A is the scatter pattern without coincidence identification and handling. FIG. 2B is the scatter pattern with coincidence identification and handling. In this example, the scatter plots correspond to DC vs. LS measurements of a high-concentration WBC specimen with 99% lymphocytes.

As discussed above, hematology analyzers utilize positional information, e.g., based on DC, RF, LS and ALL measurement parameters, to differentiate types of blood cells (e.g., particles). A peak measurement of a signal corresponding to each cell can be used to retrieve positional information. However, coincidence distorts the peak measurements, which can cause a representation of the cell to be in an incorrect location on corresponding scatter plots and histograms. This degradation of the data pattern becomes more prevalent as the sample concentration increases. For example, a diluted particle sample 103 with a higher particle concentration will, in general, result in a higher rate of coincidence, and hence more distorted data than a diluted particle sample 103 with a lower particle concentration.

In FIGS. 2A and 2B, the marked bounding rectangles, rectangles 202 and 204 respectively, are locations where lymphocytes are expected to be present. FIG. 2A shows a substantial number of lymphocytes inaccurately placed out of rectangle 202, which can easily be misclassified as other types of WBC. In contrast, in FIG. 2B, the misplaced lymphocytes are remarkably reduced because those misplaced lymphocytes were actually coincident particles that are eliminated by coincidence identification and handling, according to an embodiment of the present invention.

Figure 3:
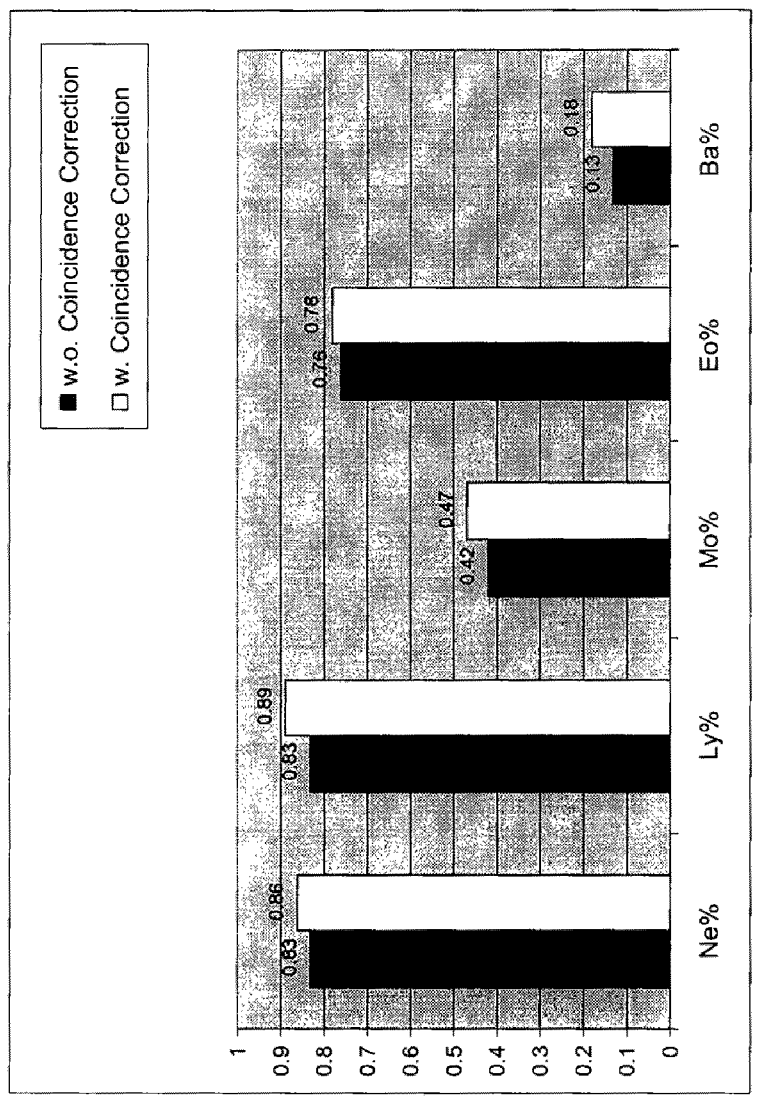
FIG. 3 illustrates a bar graph displaying a comparison of the results achieved by an embodiment of the present invention.

FIG. 3 illustrates graphs showing exemplary improvement in clinical accuracy yielded by an embodiment of the present invention. For example, a comparison of the results of a 5-part Differential test to the manual Differential results on a reference data set with and without coincidence identification and handling are shown, according to an embodiment of the present invention. The comparison is based on the percentages of neutrophils, lymphocytes, monocytes, eosinophils, and basophils, and quantized with correlation with the manual Differential. As can be seen in this example, coincidence identification and handling improves the accuracy for all five white blood sub-populations. In addition to the accuracy improvement, the coincidence identification and handling improves the number of samples flagged as indeterminate requiring to be rerun. For example, in the same dataset, the number of flagged samples is reduced by 24.5% from 351 to 265 due to applying the coincidence identification and handling according to an embodiment of the present invention.

FIGS. 4A and 4B graphically illustrate the results when an embodiment of the present invention is used to reduce the impact of coincidence caused by unlysed particles. Some hematology tests require lysing of the particle sample to remove unwanted particles from a sample prior to analysis. For example, a 5-part Differential test requires the removal of dominating red blood cells in order to precisely count and differentiate subtypes of white blood cells. However, some abnormal samples are resistant to the lysing, and cause excessive unlysed debris in the 5-part Differential scatter plots. Due to the relatively large difference in concentration between red blood cells and white blood cells in these samples, the unlysed debris often pass through the measurement region coincidently. Thus, using an embodiment of the present invention, substantially eliminating coincident particles can reduce inaccuracies caused by unlysed debris. For example, by applying the coincidence identification and handling according to an embodiment of the present invention to a reference data set, the average of the percentage of unlysed debris with respect to the white blood cells is reduced from 95% to 64%.

In FIGS. 4A and 4B, the DC vs. LS scatter plots for a sample with unlysed debris are shown. When there is no coincidence identification and handling applied, the unlysed debris interferes with the lymphocytes and results in erroneously classifying 48% of the cells as lymphocytes. For example, in FIG. 4A red blood cells and lymphocytes populations appear without a clear separation in area 401. On the other hand, FIG. 4B graphically shows results when using coincidence identification and handling which removes a significant amount of unlysed debris so that the gating between the lymphocytes and debris is substantially improved, e.g., red blood cells 402 and lymphocytes 403 are clearly separated. In this example, the coincidence identification and handling yields 7.2% lymphocytes, which is very close to the reference of 9%.

Method for Determining Coincident Particles

Figure 5:
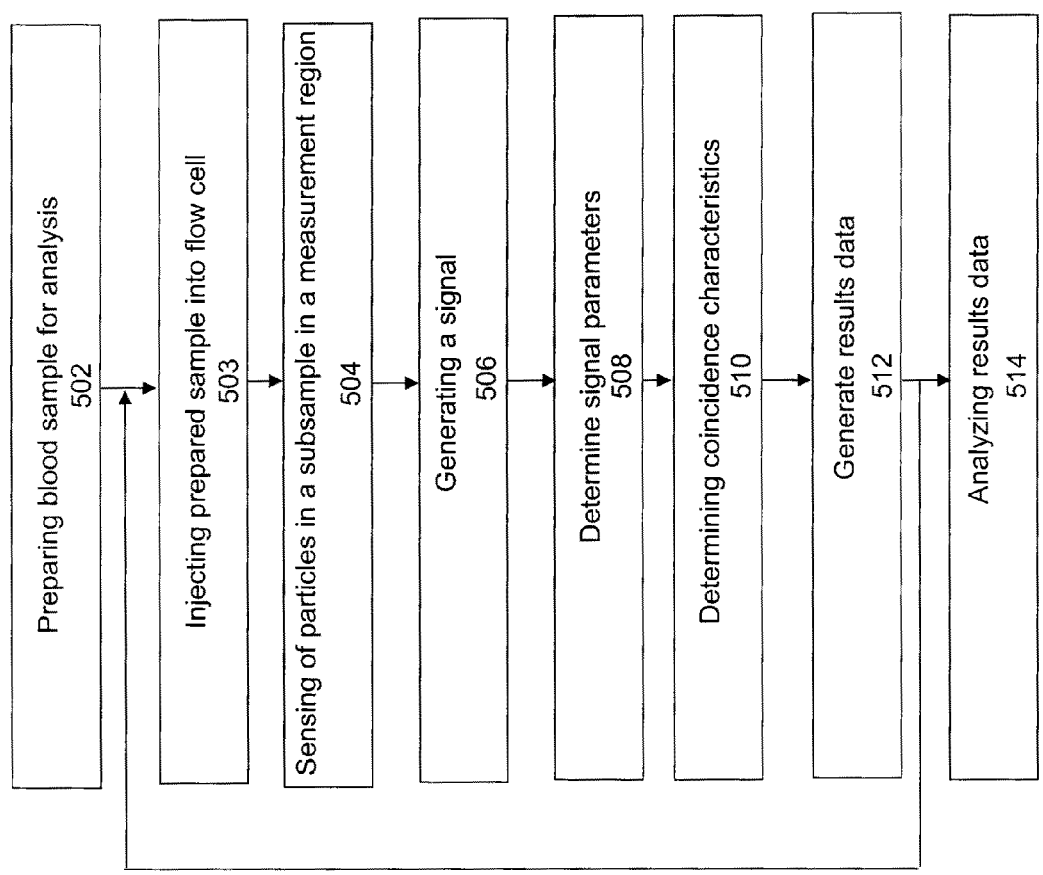
FIG. 5 is a flowchart illustrating steps in analyzing a sample of particles, according to an embodiment of the present invention.

FIG. 5 is a flowchart of a method 500 to detect and handle coincident particles, according to an embodiment of the present invention. For example, method 500 can be performed using the device of FIG. 1A, which is referenced in the description of method 500 below.

In step 502, a sample is prepared for analysis in a particle analyzer. For example, as discussed above, in hematology analysis a blood sample may be lysed to remove red blood cells prior to a 5-part Differential test for white blood cells. The preparation step may also include adding a diluent to the sample and a provision of a sheath fluid to facilitate the flowing of the sample through a flow cell, for example, flow cell 108.

In step 503, the prepared particle sample is injected into the flow cell at a constant rate. For example, this can be done using a process such as hydrodynamic focusing to ensure substantial constant fluid velocity and constrain the particles within the sheath fluid through the flow cell.

In step 504, particles in a measurement region are detected. For example, as a sub-sample of the particle sample prepared in step 502 flows through the measurement region of a flow cell, a sequence of signal pulses are generated based on a sensing of one or more particles within a measurement region, for example, measurement region 120 of flow cell 108. In one example, the sensing of particles is based on one or more of electrical or optical measurement devices that include corresponding probes and sensors, for example, probes 112 and sensors 114. For example, considering an electrical measurement device, a DC measurement parameter or electrical resistance measurement parameter can be used to detect the volume of particles, and/or an RF measurement parameter may correspond to a number of characteristics of the particles. A laser source and corresponding detectors, as discussed with regard to FIG. 1A, can comprise an optical measurement device and can be used to determine particle characteristics based on measurement parameters including LS and ALL. In another embodiment, an acoustic measurement device may be used. For example, an ultrasound source and corresponding sensors can comprise an acoustic measurement device. Herein below, the description focuses primarily on detection using a DC measurement parameter, but other measurement schemes are contemplated within the scope of the embodiments of this invention.

In step 506, a signal corresponding to the presence of the particle in the measurement region is produced. For example, using a sequence of signal pulse measurements generated by sensing the particle as the particle passes through the measurement region. Signals as shown in FIG. 1B or 1C can be representative of the signal produced in this step.

Figure 6:
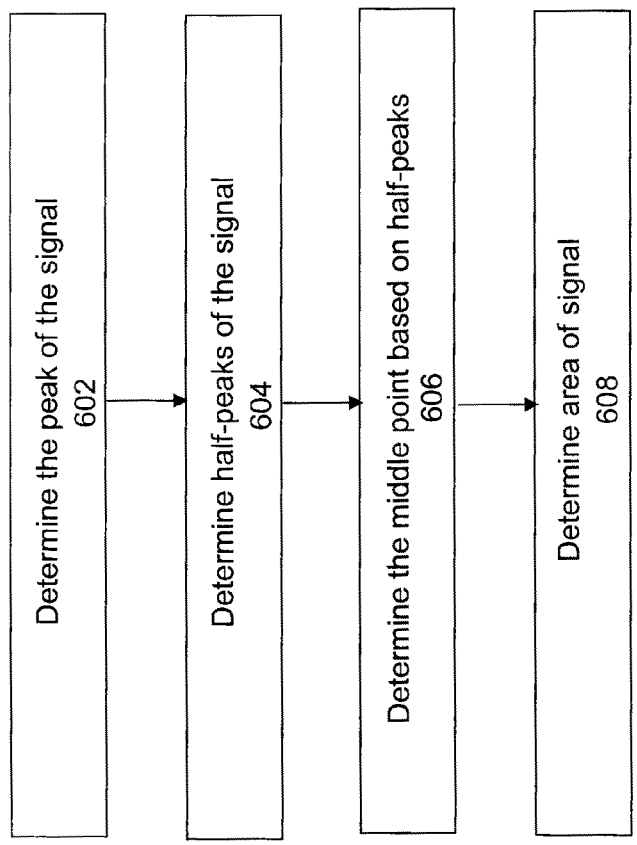
FIG. 6 is a flowchart detailing the processing involved in the determining signal parameters of FIG. 5, in an embodiment of the present invention.

In step 508, various parameters are determined based on the generated signal. For example, as shown in FIG. 1B, a peak 152 of the signal is determined. In one embodiment of the present invention, first and second points on the signal 150 having a value that correspond to a predetermined portion of the peak value are determined, the first point being on the rising part of signal 150 and the second point being on the decreasing part of signal 150. More precisely, the first point is located on the temporally first occurring rising part of signal 150 corresponding to the predetermined portion of the peak value and the second point is located on the temporally last occurring decreasing part of signal 150 corresponding to the predetermined portion of the peak value. For example, first and second points may be half-peak points 154 and 156 of signal 150, or half-peak points 164 and 166 of signal 160. Based on the first and second points, a center-point corresponding to the value of the signal at the midpoint (H50) of the time interval between the first and second points (T50) is determined. In another embodiment, the area of the signal is determined. Specifically, the area represented by the signal representing the entire duration of the particle in the measurement region is determined. For example, as shown in FIG. 6, discussed in detail below, exemplary steps are discussed for determining the parameters mentioned. Example signals representing one or more particles in the duration of its presence in a flow cell are provided in FIGS. 1B and 1C. The parameters determined using the signal are described in detail with respect to FIGS. 1B, 1C, and 7.

In step 510, coincidence characteristics of the sub-sample are determined. For example, event data, i.e., data corresponding to the detected particles and other parameters determined based the signal in step 508 is received at analyzer 122 from signal processor 118. Analyzer 122 can then determine coincidence characteristics of the sub-sample based on the received data. It should be understood, however, that the determining of the signal parameters and determining of coincidence can be distributed differently between signal processor 118 and analyzer 122.

For example, based on the parameters determined from the signal, the peak and one or both of the center-point and the first and second points of the signal, it is determined if the sub-sample includes coincident particles. A flowchart illustrating the detailed processing involved in step 510 is presented in FIG. 8. The determination of whether the sub-sample includes coincident events is described in detail with respect to FIG. 8.

In step 512, results data is generated based on the coincident events and non-coincident events (i.e., events other than the coincident events). In one embodiment, the data characteristic of the coincident events is discarded. Therefore, the results data will not include any events detected as coincident. In another embodiment, for each detected coincident event, a particle count is adjusted to account for the coincidence. For example, every sub-sample detected to have a coincidence may be considered to have a two particle coincidence, and the event count or particle count may be incremented accordingly. Adjusting the particle count in this manner can reduce the error in the count when compared with discarding the coincident sample.

In step 514, it is determined whether an entire sample has been measured. If no, method 500 returns to step 503. Otherwise, the results data collected is analyzed in step 514.

In one embodiment, the results data may be used to generate a display, for example, a scatter plot corresponding to the results data. The scatter plot would have increased accuracy and less noise because the coincident events would be substantially reduced. An example scatter plot where coincident events were removed is shown in FIG. 2B, which can be compared to when coincident events are not removed, which is shown in FIG. 2A.

In another embodiment, the results may be reported as event or particle counts adjusted in accordance with the number of coincident events that were determined using method 500.

In yet other embodiments, the results data may be transmitted to another device, including but not limited to a storage device, for storage and/or subsequent analysis.

FIG. 6 illustrates a process 600, for example sub-steps involved in the processing of step 508, according to an embodiment of the present invention. In step 602, a peak of the signal is detected, for example peak 152 of signal 150. As discussed above, the peak measurement can be considered to be representative of particle characteristics. For example, if a single particle passes through a DC measurement region, the recorded peak is proportional to the physical volume of the particles, according to the Coulter Principle. Conventionally, only the peak measurement is captured in some hematology analyzers because the peak value, by itself, is sufficient to describe certain characteristics of particles. When no coincident particles are present, the signal generally comprises a single peak. However, as discussed above with respect to FIG. 1C, a signal may have more than one peak when coincident particles are detected in the sub-sample. Signal 160 has two peaks 162A and 162B, which indicate there may be coincident particles. Peak 162A, more specifically the maximum peak of signal 160, can be determined by keeping track of the highest value of the signal.

In step 604, two points, first and second points, having a signal value corresponding to a predetermined portion of the peak, are determined. For example, the predetermined portion of the peak may be 50%, and two half-peak points can be found, such that the first half-peak point 164 is before and the second half-peak point 166 is after the peak 162A as described above with respect to FIG. 1C. The time interval between the first and second half-peak points is referred to as T50.

In step 606, a center-point 167 between the first and second points is determined. The signal value at the center point 167 of the first and second half-peak points is referred to as H50. Note that when there is no coincidence, as shown in FIG. 1B, the center point of the half-peak points 154 and 156 can overlap with peak 152.

Figure 7:
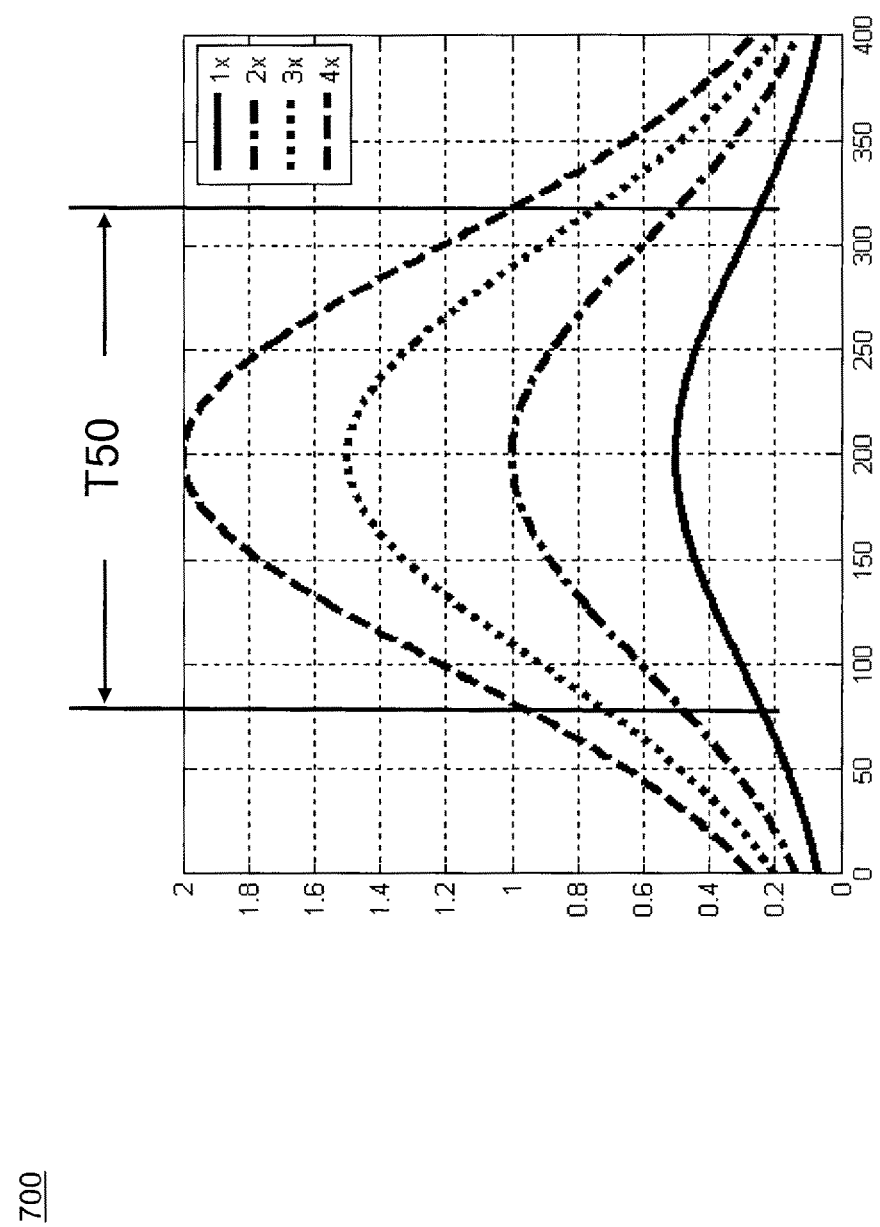
FIG. 7 illustrates a substantially constant property of one measurement (T50) in non-coincident signals, as the size of the particle increases, according to an embodiment of the present invention.

FIG. 7 illustrates a substantially constant property of one measurement (T50) in non-coincident signals as the size of the particles increases, according to an embodiment of the invention. As noted previously, the T50 is the time interval between two half-peak points on a signal. Every point on the signal represents the intensity of interaction of the measurement parameter (e.g., DC) and particle at the corresponding location in a measurement region. When the particle volume is small compared with the DC measurement region volume, the intensity is approximately proportional to the particle volume. When a larger particle passes through the measurement region, every point on the signal is increased proportionally and the half-peak points remain at same temporal points while the amplitude is enlarged compared with a smaller particle. In other words, T50 remains substantially constant regardless of particle size as long as the particles pass through the measurement region independently without coincidence. Plot 700 shows that T50 remains substantially constant temporally for various sizes of particles without coincidence. The substantially constant property of T50 for single non-coincident particles of varying sizes enables the determination of a threshold T50 value to identify coincident particles.

The H50 measurement largely depends on symmetry of the signal shape. If a signal is symmetrical and unimodal, its H50 is equal to its peak. If a signal is unimodal but asymmetrical, its H50 is less than its peak. If a signal is bimodal, its H50 is usually located in the mid-valley region in the bimodal signal and its H50 is significantly less than the peak. If a signal is multimodal, which can happen when more than two particles flow through the measurement region simultaneously, the situation is more complicated and unpredictable. However, there is a very high probability that the H50 is less than the peak in this situation. Also, coincidence of more than two particles is relatively infrequent in hematology analyzers and flow cytometers that use hydrodynamic focusing to inject the particle sample into the flow cell and can generally be ignored.

Note that for ease of reference, the term T50 is used to refer to the temporal distance between the first and second points when the first and second points are chosen to have any predetermined value corresponding to a portion of the peak value. Likewise, the term H50 is used to refer to the signal value at the mid-point of the T50 region.

In step 608, the area of the signal is determined. For example, the area of signal 160 corresponding to the entire duration in which the particle is in the measurement region, specifically in the time interval between when the particle entered measurement region 168 to when it exited 169. In one example, the area can be determined as the integral of signal 160. If a bigger particle passes through the measurement region, each point on the signal increases proportionally. If more than one particle passes through the aperture, the area of the superimposed signals is equal to the sum of the areas of all individual signals. However, the signal area may be sensitive to shape of a particle and orientation of the particle as it passes through the measurement region. Compared to the area of the signal, the T50 of the signal provides a more robust representation of the particle being analyzed. It should also be noted that except for perfectly coincidental particles, the peak does not have the additive property.

Figure 8:
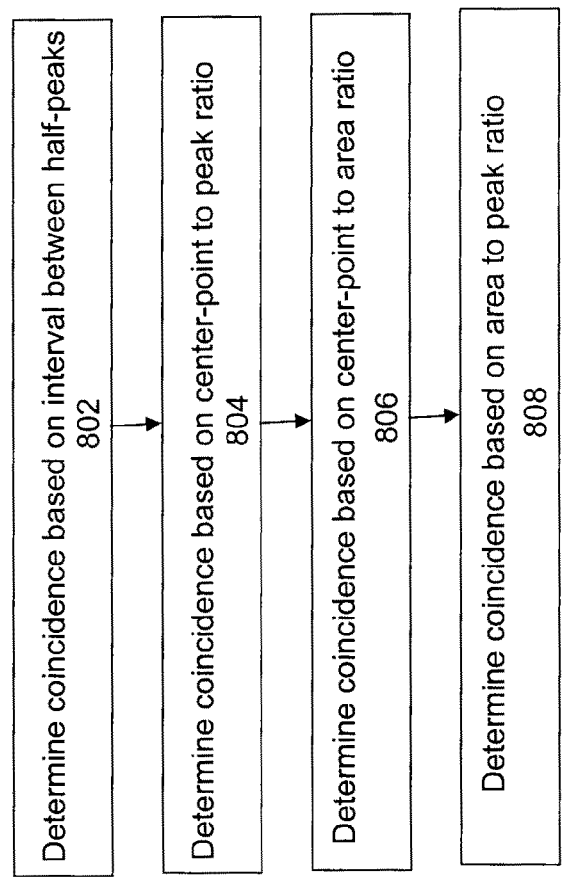
FIG. 8 is a flowchart showing steps in determining characteristic measurements of coincidence, according to an embodiment of the present invention.

FIG. 8 is a flowchart showing a process 800, for example determining coincidence characteristics in step 510, according to an embodiment of the present invention. In step 802, the T50 parameter is compared to a predetermined T50 threshold value. If the T50 value is greater than the predetermined T50 threshold value, then the signal is considered to include a coincidence. The T50 threshold value can be predetermined for each particle analyzer and associated test conditions based on the analysis of reference particle samples.

FIGS. 9, 10, 11 and 12 are graphs illustrating characteristics of particle parameters, according to an embodiment of the present invention. For example, the line represent signal measurements of non-coincidental particles over a size range of 0.2 to 0.8 in a normalized scale. The circles and the dotted-line represent the signal measurements of two 0.4 size coincident particles whose separation is adjusted by small increments of time. Because these two particles pass through the measurement region in close proximity to each other, the observed peak is not necessarily 0.4 due to waveform superposition. The circles represent the signal measurements of two equal-sized before-bifurcation particles. The dotted-line represents the signal measurements after-bifurcation.

Figure 9:
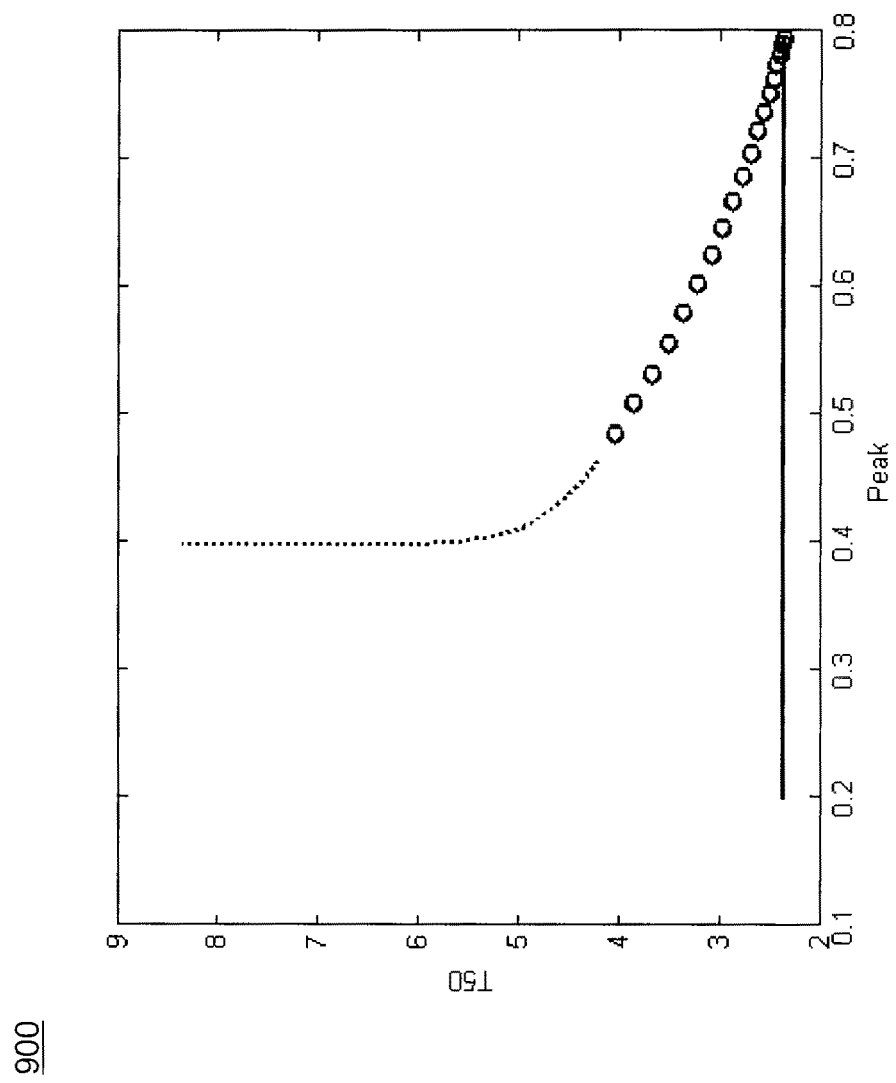
FIGS. 9, 10, 11 and 12 are graphs illustrating particle parameters, according to an embodiment of the present invention.

FIG. 9 shows a T50 vs. peak plot 900, according to an embodiment of the present invention. The single-particle signals have a constant T50 regardless of the size difference, illustrated by the horizontal line representing single-particles. The before-bifurcation coincidence pulses, shown with the circles, exhibit elevated T50s even though they are still unimodal. This is because the signals are distorted due to superposition of two individual signals. Once the coincidence becomes after-bifurcation, T50 increases dramatically, as illustrated by the dotted-line. The above observations indicate that T50 is able to differentiate both before-bifurcation and after-bifurcation coincident events from the non-coincident events. The T50 threshold value can be determined, based on the size of the particles being analyzed, to be above the value of the single particles (line in plot 900) and below the value of the corresponding coincident particle value (lower of the dotted-line or circles in plot 900).

In step 804, a ratio of the center-point of the first and second portion of the peak points to the peak (i.e., H50-to-peak ratio) is determined or computed. The H50-to-peak ratio is then compared to a predetermined threshold H50-to-peak ratio. If the H50-to-peak ratio is less than the threshold, then the signal is determined to indicate an after-bifurcation coincidence. The threshold H50-to-peak ratio can be predetermined for each particle analyzer and associated test conditions based on the analysis of reference particle samples.

Figure 10:
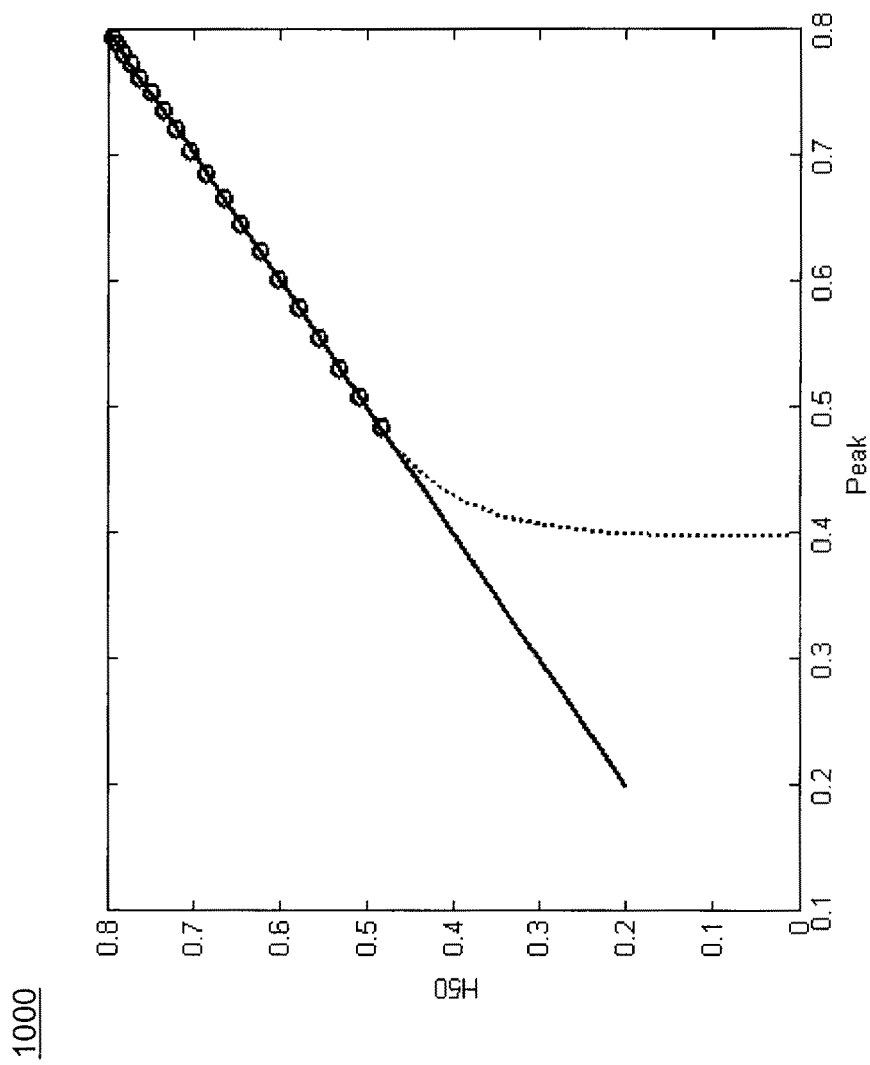

In the H50 vs. peak plot 1000 of FIG. 10, there is a diagonal line because the H50 and Peak remain equal for single-particle signals. The circles overlap with the line whenever two equal-size before-bifurcation coincident particles form a symmetrical, unimodal signal and have same H50s and peaks. This means that the H50 is incapable of differentiating before-bifurcation coincident and non-coincident signals. However, the dotted-line is clearly separate from the line, implying that the H50 can be used to distinguish the after-bifurcation coincidence signals from non-coincidence signals. In the case of two different-sized before-bifurcation coincident particles, the superposition of two particles creates a level of asymmetry, and hence makes the H50 measurements different from the peak measurement. However, this difference is usually not significant.

In step 806, a ratio of the center-point of the first and second portion of the peak points to the area (i.e., H50-to-area ratio) is determined or computed. The H50-to-area ratio is then compared to a predetermined threshold H50-to-area ratio. If the H50-to-area ratio is less than the threshold, then the signal is determined to indicate an after-bifurcation coincidence. The threshold H50-to-area ratio can be predetermined for each particle analyzer and associated test conditions based on the analysis of reference particle samples.

Figure 11:
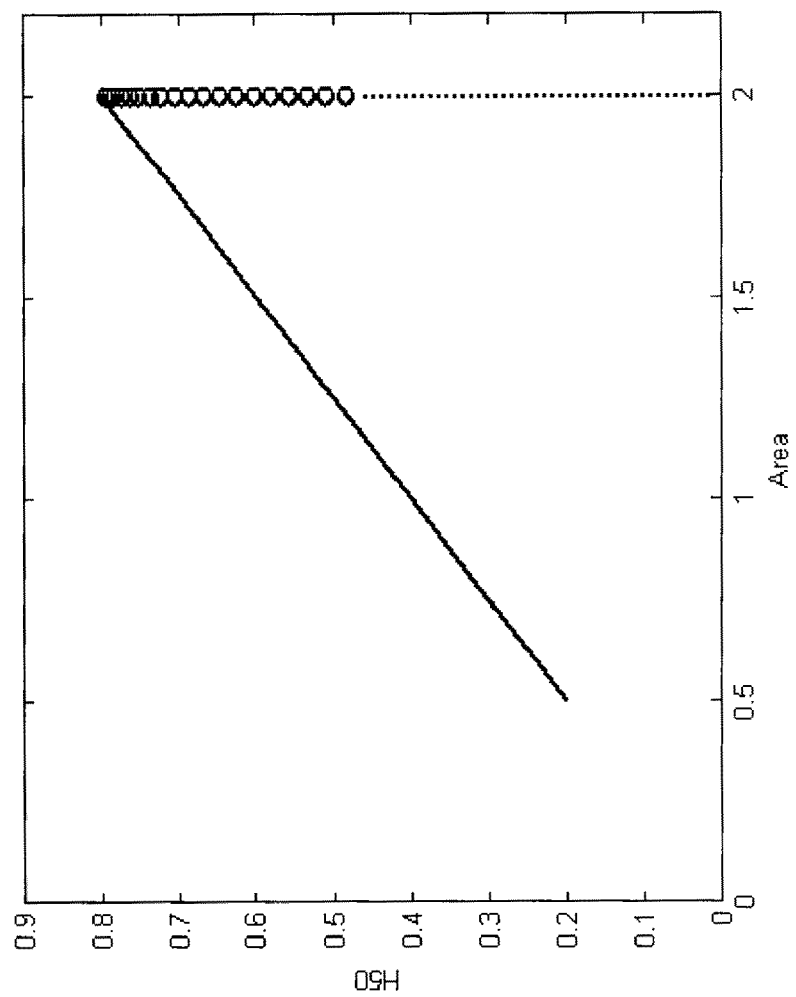

In the H50 vs. area plot 1100 of FIG. 11, there is a straight diagonal line because the H50-to-area ratio remains constant for single-particle signals. The circles and the dotted line show that area of two-particle coincident signals remain constant. This can be explained by the fact that the area of two particles is equal to the sum of the area of each particle as long as these two particles go through the measurement region coincidently. Thus, all single particles form a diagonal through the origin on the area vs. area scatter plot and have a constant H50-to-area ratio, while the coincident particles locate to the right of and below the single-particle line on the scatter plot and their H50-to-area ratios are lowered. This can imply that the H50-to-area ratio can be used to distinguish coincident pulses (including both before-bifurcation and after-bifurcation types) and non-coincident pulses.

In step 808, an area-to-peak ratio is determined. Based on whether the area-to-peak ratio is greater than a predefined threshold, this signal is either before-bifurcation or after-bifurcation coincident signal. The threshold area-to-peak ratio can be predetermined for each particle analyzer and associated test conditions based on the analysis of reference particle samples.

Figure 12:
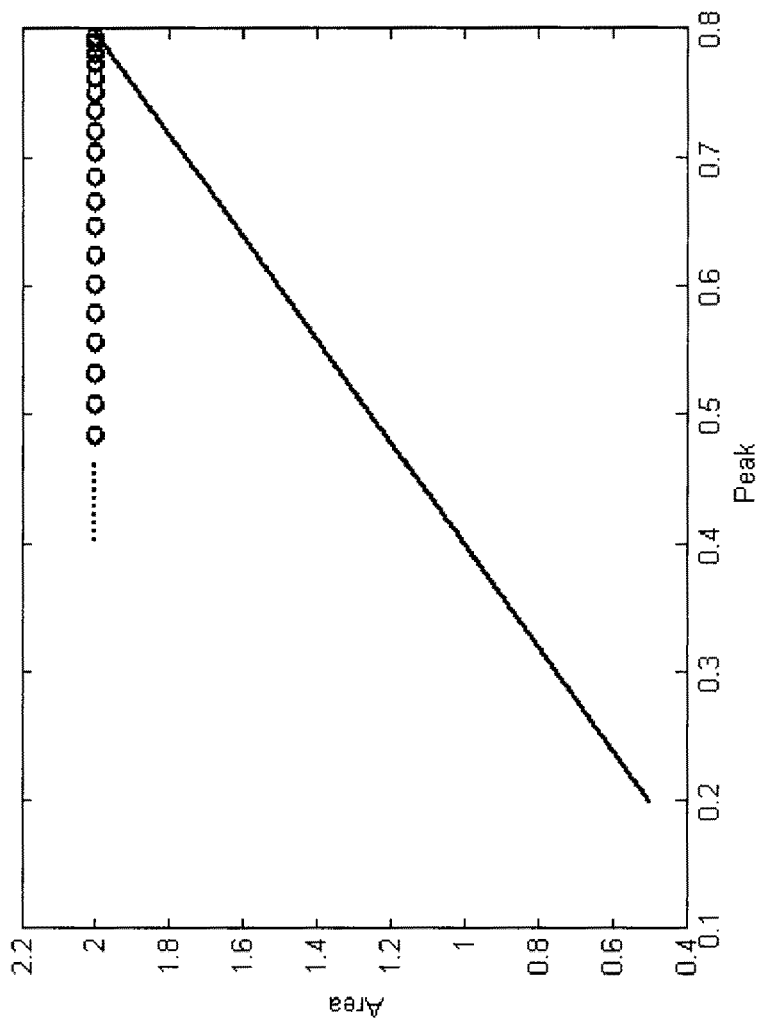

In the area vs. peak plot 1200 shown in FIG. 12, the area of the single-particle signal (shown with the line) increases proportionally to the peak. On the other hand, the area of two-particle coincident signals, regardless of before-bifurcation (shown with the circles) or after-bifurcation (shown with the dotted line), remains constant, which is twice the area of 0.4-peak signal. This can be explained by the fact that the area of two particles is equal to the sum of the area of each particle as long as these two particles go through the measurement region coincidently. Thus, all single particles form a diagonal through the origin on the area vs. peak scatter plot and have a constant area-to-peak ratio, while the coincident particles locate to the left of and above the single-particle line on the scatter plot and their area-to-peak ratios are elevated. This can imply that the area-to-peak ratio can be used to distinguish coincident pulses (including both before-bifurcation and after-bifurcation types) and non-coincident pulses.

It should be noted that other embodiments of the present invention can use one or more of the methods of determining coincidence events described above. In general, the comparison of T50 to a predetermined threshold provides the most robust results. However, some embodiments may also include coincidence determination through H50-to-peak and/or area-to-peak, to increase the reliability of the determination.

Example Application to a 5-Part Differential Test

Figure 13:
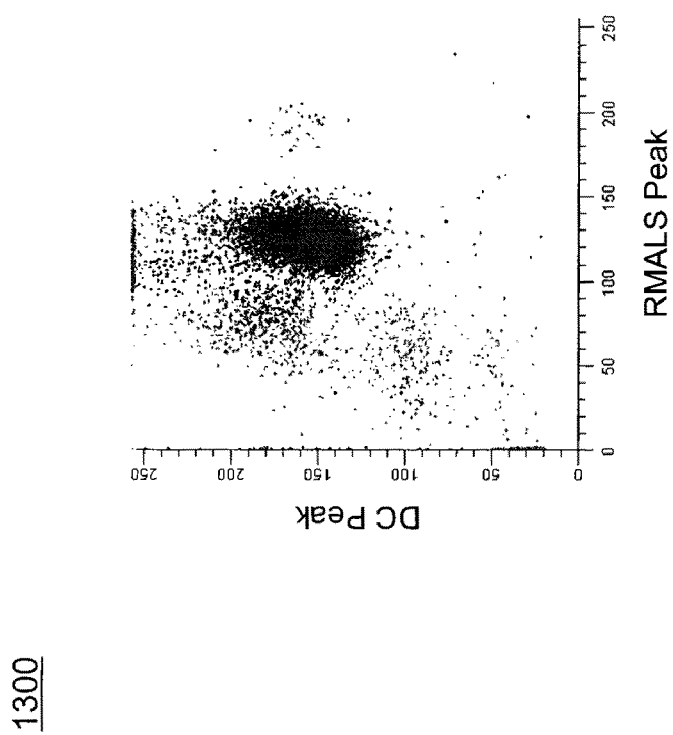
FIGS. 13, 14, 15, 16 and 17 are scatter plots illustrating various effects of coincidence identification, according to an embodiment of the present invention.
Figure 14:
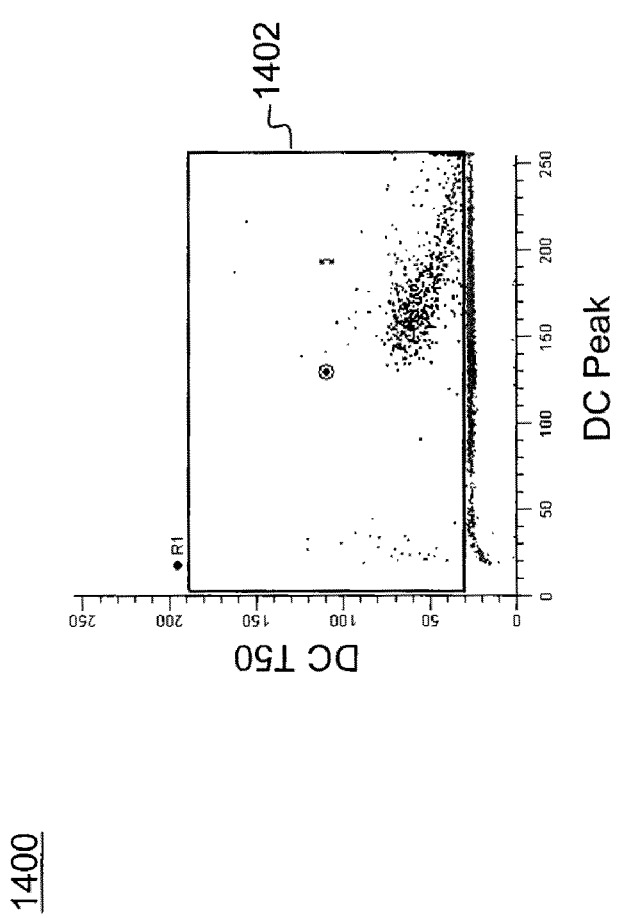

FIGS. 13, 14, 15, 16 and 17 illustrate coincidence identification on a blood specimen that contains blood cells of various sizes, according to one or more embodiments of the present invention. The specimen has normal white blood cell concentration, which implies a relatively low level of coincidence. In FIG. 13, a 5-part Differential scatter plot 1300 having axis corresponding to the DC peak and LS peak is shown. The majority of T50 values on this real specimen are constant, forming a straight horizontal line in FIG. 14. The rest (located within rectangle 1402) have larger and irregular T50 values, which correspond to signals identified as before-bifurcation or after-bifurcation coincident signals. FIG. 14 corresponds to the simulated results for T50 vs. peak (FIG. 9).

Figure 15:
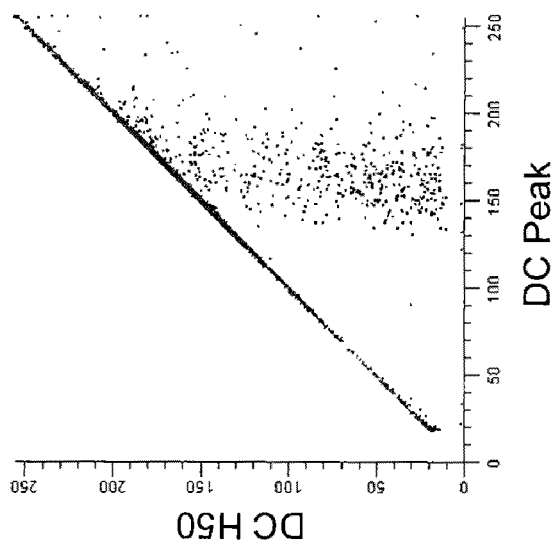

FIG. 15 shows the resulting scatter plot 1500 when coincident signals identified with the T50s are projected into DC H50 vs. peak space. The majority of the coincident pulses identified with the T50s exhibit smaller H50s compared to the corresponding peaks, which indicate that those are after-bifurcation coincident pulses. Some of the coincident pulses identified with the T50s have equivalent H50s and peaks. Those are before-bifurcation coincident pulses, which can be discriminated with the T50 or area-to-peak ratio but not with the H50.

Figure 16:
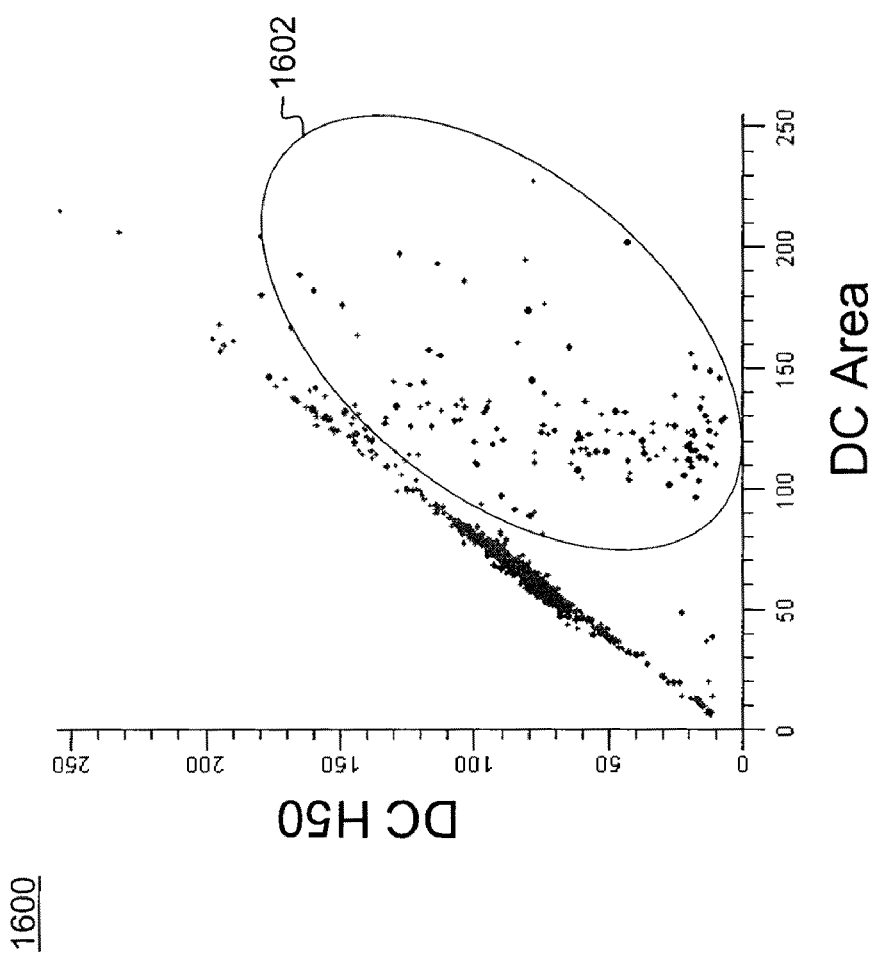

The DC H50 vs. DC area scatter pattern 1600 shown in FIG. 16 is composed of a events forming a diagonal going through the origin and other scattered points below the diagonal. The former represents the non-coincident white blood cells. The latter forms a "cloud" with lower H50-to-area ratios and may represent coincident particles (1602).

Figure 17:
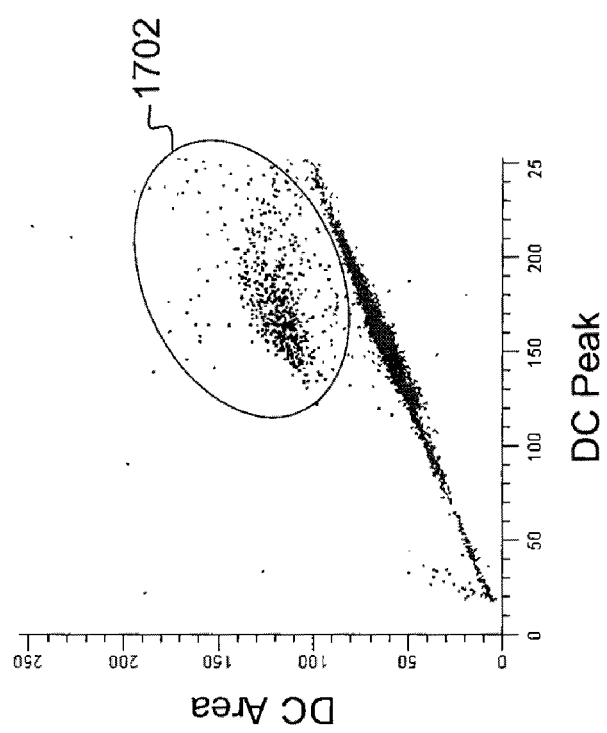

It can also be seen in FIG. 17 that the DC area vs. peak scatter pattern 1700 is composed of a diagonal going through the origin and other scattered points above the diagonal. The former represents the non-coincident white blood cells. The latter forms a "cloud" with higher area-to-peak ratios and may represent coincident particles. If the coincident points (1402) in FIG. 14 are compared to coincident points (1702) in FIG. 17, we can see that the results from T50 thresholding and area-to-peak-ratio thresholding agree with each other.

Other Example Embodiments

In another embodiment of the present invention, multiple measurement parameters may each be independently used to determine coincidence events. Having independently determined coincidence using multiple measurement parameters, the results may be correlated to arrive at a final determination. Such a method may offer a more robust determination of coincident events in which the effects of sensitivities of each measurement parameter in detecting coincident events in various conditions is reduced. For example, a final determination of a coincidence may be made for an event that is flagged as coincident by at least one of the measurement parameters.

Figure 18:
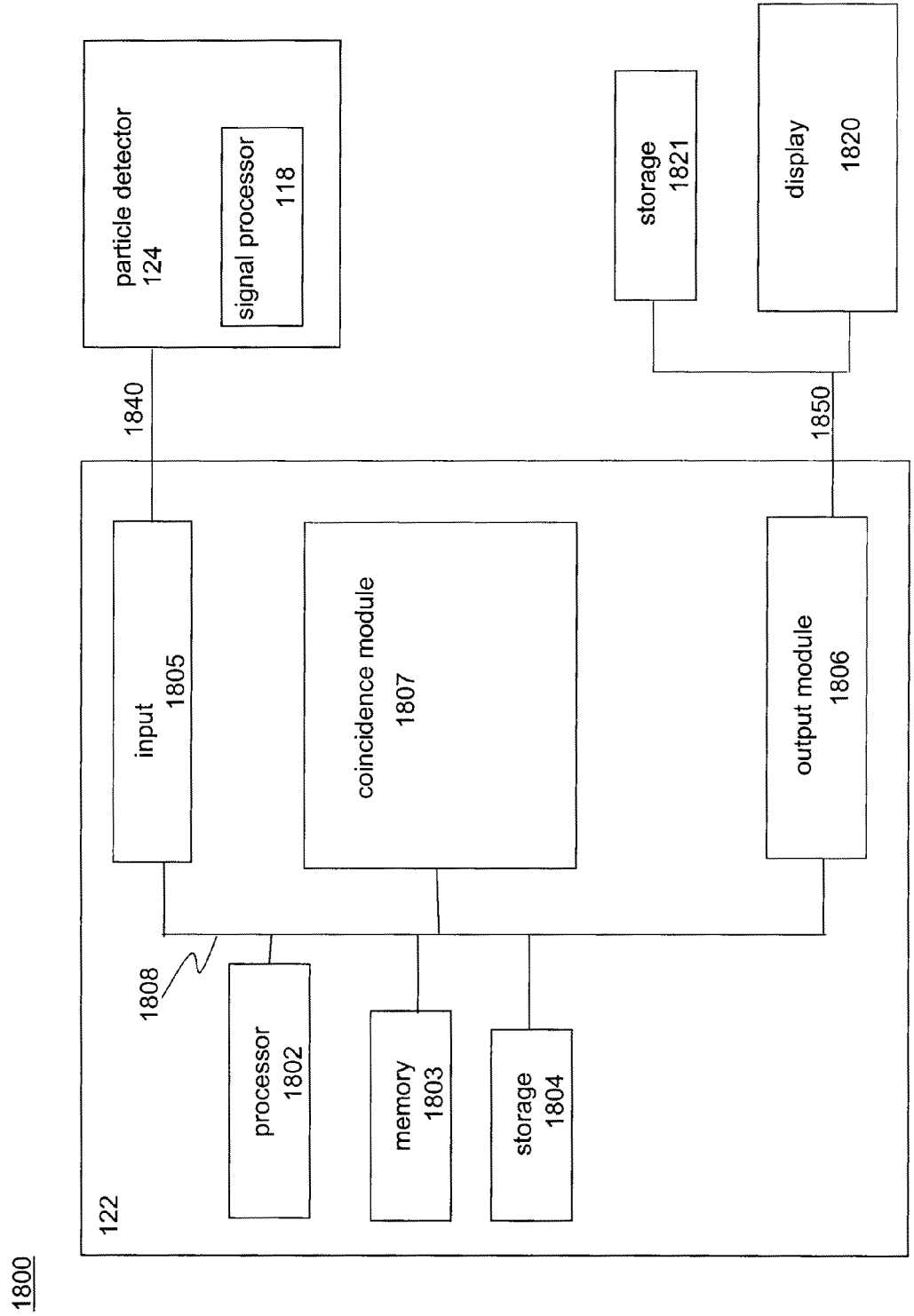
FIG. 18 shows a detailed view of an analyzer module and a system, according to one embodiment of the present invention.

FIG. 18 shows another embodiment of the present invention. A system 1800 according to an embodiment of the present invention, includes a particle detector 124 coupled to an analyzer 122. Analyzer 122 may also be coupled to a display 1820 and storage 1821. Particle detector 124 detects particle events using one or more measurement parameters, and includes signal processor 118 that processes the detected measurement parameters to construct a signal for each particle event representing the duration of that particle in a measurement region. Signal processor 118, as noted above, determines a peak and one or more of a signal-area or a T50 and H50 parameter for each signal. The instructions for assembling the signal corresponding to the duration of a particle in the measurement region and the determining of the parameters corresponding to that signal can be implemented in any suitable programming language including a hardware description language (HDL), Assembly, C and C++, and may include one or more of hardware, firmware, or software components. In one embodiment, the assembling of the signal and determination of the signal parameters such as peak, H50, T50 and area can be performed in a field programmable gate array (FPGA) and the threshold comparisons for coincidence can be performed in software.

As described with respect to FIG. 1 above, analyzer 122 may either be located within particle analyzer 100 or be located separately coupled to particle detector 124 through a communications medium 1840. Analyzer 122 receives event data corresponding to the signal generated by each particle detected by particle detector 124. The event data can include positional data as well as computed parameters including the peak, signal-area, T50 and H50 measurements for the corresponding signal.

Analyzer 122 includes components including a processor 1802, a memory device 1803, a storage device 1804, an input device 1805, an output device 1806, a coincidence module 1807 and a communications device 1808. Processor 1802 can be any microprocessor or other processor capable of executing processing instructions. Memory device 1803 can include a random access memory. Storage device 1804 includes a persistent storage medium such as a flash memory or hard disk. Processor 1802 executes the instructions for receiving event data from particle analyzer, processing the received data and outputting the processed results data. Memory device 1803 and storage device 1804, provides any temporary or permanent memory and storage requirements of processor 1802. Communication device 1808 interconnects components of analyzer 122 to each other, and may include a communications medium, including but not limited to a peripheral component interconnect (PCI) bus or Extended Industry Standard Architecture (EISA) bus. Input device 1805 can include connectivity to particle analyzer 100 through connection device 1840 and the capability to receive data including event data from particle analyzer 100. Connection 1840 can be a network connection device such as an Ethernet or a device internal connection device such as a PCI or EISA bus.

Coincidence module 1807 includes the functionality to process the event data including the positional data and the corresponding signal parameters received from the particle detector 124 to determine coincidence in each event. For example, as described above, one or more of the peak, signal-area, T50 and H50 parameters can be used by coincidence module 1807 to determine the existence of a coincident event in the corresponding sub-sample of the particle sample. In some embodiments, coincidence module 1807 can receive signal parameters independently determined using multiple measurement parameters, and correlate the different determinations to arrive at a final determination regarding coincidence in the corresponding event.

Output module 1806 includes the functionality to handle the coincident events in a way appropriate for the application. In one embodiment, output module can adjust one or more particle counts by accounting for coincidence events. For example, each coincident event may cause a corresponding particle count to be incremented by 2 instead of 1. In another embodiment, output module 1806 can remove events determined to be coincident. For example, results data can be generated excluding any of the events detected as coincident. The instructions for achieving the functionality of input module 1805, coincidence module 1807 and output module 1806 can be implemented using hardware, firmware, software or a combination thereof.

Output module 1806 is coupled using a communications device 1850 to display 1820 and/or storage device 1821. Communications medium 1850 can include network connection such as an Ethernet or a device internal connection method such as a PCI or EISA bus. The results data from output module 1806 is transported to display 1820 to be displayed and analyzed by an operator. For example, display 1820 may illustrate the results data in the form of a scatter plot (an example of which is shown in FIG. 2B). In another embodiment, the results data may simply be stored in an external storage device 1821 for subsequent processing and analysis.

In this disclosure, methods and systems were disclosed that can improve the accuracy particle analysis, including blood sample analysis, through the identification and handling of coincidence events that occur in the detection of events. The disclosed methods and systems yield substantial improvements over current methods and systems and can lead to significant improvements in the analysis of particle analyzer data. Persons skilled in the art will understand that the techniques disclosed herein can be applicable a number of biological or industrial particles and is also applicable to a number of detection methods using electrical, optical or acoustic measurement devices.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A method of analyzing particles in a particle analyzer, the method comprising:
preparing a fluid sample containing particles for analysis in the particle analyzer;
sensing signals using an electrical or optical measurement device, each of the signals corresponding to one or more events detected in a sub-sample of the fluid sample flowing through a measurement region in the particle analyzer;

using measurements of at least one measurement parameter from at least one said measurement device to identify a peak for each of the signals from the at least one said measurement device;

using the measurements of the at least one measurement parameter, to identify, for each of the signals, first and second points having a signal value corresponding to a predetermined portion of the identified peak for the signal; and determining the existence of coincident events in the one or more events based on the identified peak and the identified first and second points for each of the signals generating a results data based upon the coincident events and non-coincident events of the one or more events.

2. The method of claim 1, wherein the results data does not include the coincident events.

3. The method of claim 1, further comprising:
displaying a plot of the results data, whereby the plot is substantially free of coincident event noise.

4. The method of claim 1, wherein the determining comprises:
measuring an interval between the first and second points;
comparing the interval to a predetermined threshold; and
determining the existence of the coincident events if the interval exceeds the threshold.

5. The method of claim 1, wherein the determining comprises:
measuring a center point of the signal between the first and second points and an area of the signal to determine a center point-to-area ratio of the signal;
comparing the center point-to-area ratio to a threshold ratio; and
determining the existence of the coincident events if the center point-to-area ratio is less than the threshold ratio.

6. The method of claim 1, wherein the sensing includes a DC measurement parameter.

7. The method of claim 1, wherein the sensing includes a radio frequency measurement parameter.

8. The method of claim 1, wherein the sensing includes a light scatter measurement parameter.

9. The method of claim 1, wherein the sensing includes an axial light loss measurement parameter.

10. The method of claim 1, wherein the particles comprise biological cells.

11. The method of claim 1, wherein the particle analyzer is a hematology analyzer or a flow cytometer.

12. The method of claim 1, wherein the results data includes a modified count of the one or more events, and wherein the modified count is based on the coincident events and the non-coincident events.

13. A method of analyzing particles in a particle analyzer, comprising:
preparing a fluid sample containing particles for analysis in the particle analyzer;
sensing signals using an electrical or optical measurement device, each of the signals corresponding to one or more events detected in a sub-sample of the fluid sample flowing through a measurement region in the particle analyzer;
determining the existence of coincident events in the one or more events based on measuring, for a measurement parameter from at least one said measurement device, a peak, and first and second points of each of the signals using that measurement device, wherein the first and second points have a signal value corresponding to a predetermined portion of the peak; and generating a results data based upon the coincident events and non-coincident events of the one or more events,
wherein the determining further comprises:
measuring a center point of the signal between the first and second points;
comparing a ratio comprising the center point to the peak to a threshold ratio; and
determining the existence of the coincident events if the ratio is less than the threshold ratio.

14. The method of claim 13, wherein the determining further comprises determining if the coincident events comprise a bifurcated coincident event or a non-bifurcated coincident event.

15. The method of claim 13, wherein the results data does not include the coincident events.

16. The method of claim 13, further comprising:
displaying a plot of the results data, whereby the plot is substantially free of coincident event noise.

17. The method of claim 13, wherein the sensing includes a DC measurement parameter.

18. The method of claim 13, wherein the sensing includes a radio frequency measurement parameter.

19. The method of claim 13, wherein the sensing includes a light scatter measurement parameter.

20. The method of claim 13, wherein the sensing includes an axial light loss measurement parameter.

21. The method of claim 13, wherein the particles comprise biological cells.

22. The method of claim 13, wherein the particle analyzer is a hematology analyzer or a flow cytometer.

23. The method of claim 13, wherein the results data includes a modified count of the one or more events, and wherein the modified count is based on the coincident events and the non-coincident events.

24. A system comprising:
a particle detector configured to sense signals using an electrical or optical measurement device, each of the signals corresponding to one or more events detected in a sub-sample of the fluid sample flowing through a measurement region in the particle detector; and
an analyzer configured to:
use measurements of at least one measurement parameter from at least one said measurement device to identify a peak for each of the signals from the at least one said measurement device;
use measurements of the at least one measurement parameter to identify, for each of the signals, first and second points having a signal value corresponding to a predetermined portion of the identified peak for the signal; and
determine the existence of coincident events in the one or more events based on the identified peak and the identified first and second points for each of the signals
generate results data based upon the coincident events and non-coincident events of the one or more events.

25. The system of claim 24, wherein the sensing is one of DC, light scatter, axial light loss, or radio frequency.

26. The system of claim 24, wherein the analyzer is further configured to determine the existence of the coincident events based on comparing a time interval between first and second points of the signal to a predetermined threshold.

27. The system of claim 24, wherein the analyzer is further configured to determine the existence of the coincident events based on comparing a center point-to-area ratio of the signal to a predetermined threshold ratio.

28. The system of claim 24, further comprising a display configured to display the results data.

29. A system comprising:
a particle detector configured to sense signals using an electrical or optical measurement device, each of the signals corresponding to one or more events detected in a sub-sample of the fluid sample flowing through a measurement region in the particle detector; and
an analyzer configured to:
determine the existence of coincident events in the one or more events based on measuring, for a measurement parameter from at least one said measurement device, a peak, and first and second points of each of the signals using that measurement device, wherein the first and second points have a signal value corresponding to a predetermined portion of the peak; and
generate results data based upon the coincident events and non-coincident events of the one or more events.
wherein the analyzer is further configured to determine the existence of the coincident events based on comparing a ratio comprising a center point between first and second points of the signal and a peak of the signal to a predetermined threshold ratio.

30. The system of claim 29, wherein the sensing is one of DC, light scatter, axial light loss, or radio frequency.

31. The system of claim 29, wherein the analyzer is further configured to determine the existence of the coincident events based on comparing a time interval between first and second points of the signal to a predetermined threshold.

32. The system of claim 29, further comprising a display configured to display the results data.

33. A computer-readable storage device having computer program code recorded thereon that, when executed by a processor, causes the processor to perform a method, the method comprising:
receiving signals from an electrical or optical measurement device, each said signal corresponding to one or more events detected in a sub-sample of a fluid sample flowing through a measurement region in a particle analyzer;
using measurements of at least one measurement parameter from at least one said measurement device, identifying a peak for each of the signals from the at least one said measurement device;
using the measurements of the at least one measurement parameter, identifying, for each of the signals, first and second points having a signal value corresponding to a predetermined portion of the identified peak for the signal;
determining the existence of coincident events in the one or more events based on the identified peak and the identified first and second points for each of the signals and generating results data based upon the coincident events and non-coincident events of the one or more events.

34. The device of claim 33, wherein the determining comprises:
measuring a center point of the signal between the first and second points;
comparing a ratio comprising the center point to the peak to a threshold ratio; and
determining the existence of the coincident events if the ratio is less than the threshold ratio.

35. A computer program product comprising a computer usable storage device having control logic stored therein, the control logic comprising:
a first module configured to receive signals, each said signal corresponding to one or more events detected in a sub-sample of a fluid sample flowing through a measurement region in a particle analyzer;
a second module configured, using measurements of at least one measurement parameter from at least one said measurement device, to
identify a peak for each of the signals from the at least one said measurement device,
identify, for each of the signals, first and second points having a signal value corresponding to a predetermined portion of the identified peak for the signal, and
determine the existence of coincident events in the one or more events based on the identified peak and the identified first and second points for each of the signals; and
a third module configured to generate a results data based upon the coincident events and non-coincident events of the one or more events.

36. The computer program product of claim 35, the control logic further comprising: a fourth module configured to display a plot of the results data, whereby the plot is substantially free of coincident event noise.

37. The computer program product of claim 35, wherein the second module is further configured to determine the existence of coincident events by:
measuring a center point of the signal between the first and second points;
comparing a ratio comprising the center point to the peak to a threshold ratio; and
determining the existence of the coincident events if the ratio is less than the threshold ratio.

* * * * *